United States Patent [19]

Deters et al.

[11] Patent Number: 5,186,942

[45] Date of Patent: * Feb. 16, 1993

[54] NICARDIPINE THERAPY

[75] Inventors: Joseph C. Deters, Napa; David R. Swanson, Palo Alto; Stephen C. DeRosa, Menlo Park, all of Calif.

[73] Assignee: ALZA Corporation, Palo Alto, Calif.

[*] Notice: The portion of the term of this patent subsequent to Mar. 7, 2009 has been disclaimed.

[21] Appl. No.: 793,988

[22] Filed: Nov. 18, 1991

Related U.S. Application Data

[63] Continuation-in-part of Ser. No. 524,951, May 18, 1990, Pat. No. 5,096,716, which is a continuation-in-part of Ser. No. 303,706, Jan. 30, 1989, abandoned.

[51] Int. Cl.$^5$ ............................................. A61K 9/21
[52] U.S. Cl. ................................. 424/473; 424/472; 424/468
[58] Field of Search ..................... 424/473, 468, 472

[56] References Cited

U.S. PATENT DOCUMENTS

| | | | |
|---|---|---|---|
| 2,799,241 | 6/1957 | Wurster | 118/24 |
| 3,845,770 | 11/1974 | Theeuwes et al. | 128/260 |
| 3,916,899 | 11/1975 | Theeuwes et al. | 128/260 |
| 4,063,064 | 12/1977 | Saunders et al. | 219/121 |
| 4,088,864 | 5/1978 | Theeuwes et al. | 219/121 |
| 4,200,098 | 4/1980 | Ayer et al. | 128/260 |
| 4,285,987 | 8/1981 | Ayer et al. | 427/3 |
| 4,783,337 | 11/1988 | Wong et al. | 424/468 |
| 4,892,778 | 1/9190 | Theeuwes et al. | 428/218 |

Primary Examiner—Thurman K. Page
Assistant Examiner—Leon R. Horne
Attorney, Agent, or Firm—Paul L. Sabatine; Edward L. Mandell; Jean M. Duvall

[57] ABSTRACT

A dosage form is disclosed comprising a member selected from the group consisting of nicardipine and its pharmaceutically acceptable salts for administering to a patient in need of cardio-vascular therapy.

2 Claims, 6 Drawing Sheets

FIG.13

NICARDIPINE THERAPY

CROSS-REFERENCE TO RELATED APPLICATION

This application is a continuation-in-part of application U.S. Ser. No. 07/524,951 filed May 18, 1990, now U.S. Pat. No. 5,096,716 issued Mar. 17, 1992 which application Ser. No. 07/524,951 is a continuation-in-part of application U.S. Ser. No. 07/303,706 now abandoned, filed on Jan. 30, 1989, which applications are incorporated herein by reference, and benefit is claimed of their filing dates. This application, and application Ser. Nos. 07/524,951 and 07/303,706 are assigned to the ALZA Corporation of Palo Alto, Calif.

FIELD OF THE INVENTION

This invention pertains to a dosage form comprising the beneficial drug nicardipine useful for treating cardiovascular conditions. The invention also concerns a method for treating cardiovascular conditions by administering a dosage form that delivers nicardipine at a therapeutically effective rate for the management of the cardiovascular conditions.

BACKGROUND OF THE INVENTION

The beneficial drug nicardipine, 1,4-dihydro-2,6-dimethyl-4-(3-nitrophenyl)-3,5-pyridinedicarboxylic acid methyl 2-[methyl-(phenylethyl) amino] ethyl ester and its pharmaceutically acceptable salts, is a calcium antagonist clinically useful for the treatment of cardiovascular conditions. Nicardipine is clinically useful, in a patient in need of nicardipine, for treating cardiovascular condition such as ischemia, hypertension, congestive heart failure, cerebrovascular diseases and coronary artery disease. Nicardipine reduces myocardial oxygen demand through coronary vasodilation and it has cardioprotective and vascular antispastic effects. Nicardipine's chemical structure and synthesis are disclosed in *The Merck Index*, 10th Ed., p 931, (1983). Nicardipine's therapeutic properties are disclosed in a study reported in *Clinical Therapeutics*, Vol. 10, pp 316 to 325, (1988). The drug was administered in the latter study intravenously for its cardiovascular effects.

In the light of the above presentation, it will be appreciated by the pharmaceutical and medical professions that a considerable need exists for an oral dosage form useful for administering nicardipine and its pharmaceutically acceptable salts for the management of cardiovascular diseases and for its clinical relevance. The need exists for a dosage form that can deliver the valuable drug nicardipine and its pharmaceutically acceptable salts at a rate controlled by the dosage form to a patient suffering with these conditions and in critical need of nicardipine cardiovascular therapy. The pressing demand exists also for an oral dosage form that can deliver nicardipine at a controlled rate and at a constant dose per unit time over a prolonged period of time for its beneficial hemodynamic effects, which delivery occurs substantially independent of the variable environment of the gastrointestinal tract. it will be appreciated further by those versed in the dispensing art, that such a novel and unique form that can administer nicardipine in a rate controlled dose over time, and simultaneously provide cardiovascular therapy, would represent an advancement and a valuable contribution to the arts.

OBJECTS OF THE INVENTION

Accordingly, in view of the above presentation, it is an immediate object of this invention to provide a dosage form for delivering nicardipine and its therapeutically acceptable salts in a rate controlled amount, and which dosage form substantially overcomes the deficiencies associated with the prior art.

Another object of the present invention is to provide a dosage form for administering nicardipine in a rate controlled dose over a prolonged period of time for cardiovascular therapy.

Another object of the invention is to provide a pharmaceutical dosage form that makes available sustained and controlled nicardipine therapeutic activity.

Another object of the invention is to provide a novel dosage form manufactured as an osmotic device that can administer nicardipine to a biological receptor to produce the desired pharmaceutical effects.

Another object of the present invention is to provide a dosage form manufactured as an osmotic dosage form that substantially reduces and/or substantially eliminates the unwanted influences of the gastrointestinal environment of use and still provides controlled administration of nicardipine over time.

Another object of the present invention is to provide an improvement in a dosage form for administering a member selected from the group consisting of nicardipine and its pharmaceutically acceptable salts for calcium antagonist therapy, and wherein the improvement comprises delivering a composition comprising nicardipine and its salts with two different polyethylene oxide polymers for enhancing the maximum delivery of the nicardipine and its salts from the dosage form for improved and known therapy.

Another object of the present invention is to provide a dosage form adapted for oral administration of nicardipine, which dosage form comprises a first composition and a contacting second composition that act in harmony for the rate controlled administration of nicardipine over time.

Another object of the present invention is to provide a complete pharmaceutical regimen comprising a composition comprising nicardipine that can be dispensed from a drug delivery device, the use of which device requires intervention only for initiation and possibly for termination of the regimen.

Another object of the invention is to provide a method of treating cardiovascular disease by orally administering nicardipine in a rate controlled dose per unit time to a warm-blooded animal in need of cardiovascular therapy.

Another object of the invention is to provide immediate nicardipine therapy over a prolonged period of time up to 24 hours.

Other objects, features and advantages of the invention will be more apparent to those versed in the dispensing arts from the following detailed specification, taken in conjunction with the drawings and the accompanying claims.

BRIEF DESCRIPTION OF THE DRAWINGS

In the drawing figures, which are not drawn to scale but are set forth to illustrate various embodiments of the invention, the drawing figures are as follows.

DETAILED DESCRIPTION OF THE INVENTION

Figure 1:
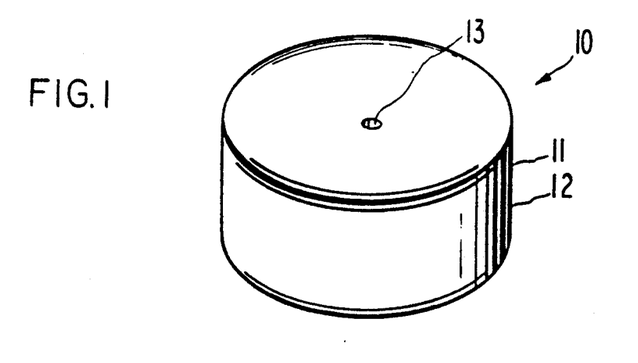
FIG. 1 is a view of a dosage form designed and shaped for orally administering nicardipine or nicardipine and its pharmaceutically acceptable salts to a gastrointestinal receptor of a warm-blooded animal.

Turning now to the drawing figures in detail, which drawing figures are an example of the dosage form provided by this invention, and which example is not to be construed as limiting, one example of the dosage form is illustrated in FIG. 1 and designated by the numeral 10. In FIG. 1, dosage form 10 comprises a body member 11 comprising a wall 12 that surrounds and encloses an internal compartment, not seen in FIG. 1. Dosage form 10 comprises at least one exit means 13 for connecting the interior of dosage form 10 with the exterior environment of use.

Figure 2:
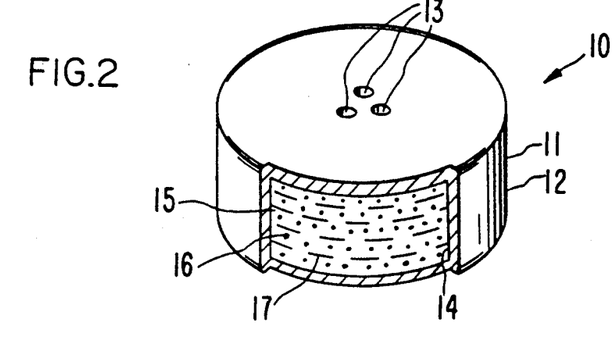
FIG. 2 is an opened view of the dosage form of FIG. 1 for illustrating the structure of the dosage form.

In FIG. 2, dosage form 10, manufactured as an osmotic device, is seen in opened view. In FIG. 2, dosage form 10 comprises body 11, wall 12, that is sectioned at 14, and which wall surrounds and defines as internal compartment 15. Wall 12 comprises at least one exit means 13 or a plurality of exit means 13 that connect compartment 15 with the exterior of dosage form 10.

Wall 12 of dosage form 10 comprises in at least a part a composition that is permeable to the passage of an exterior fluid present in the environment of use, such as water or a biological fluid. Wall 12 is substantially impermeable to the passage of nicardipine and other ingredients present in compartment 15. Wall 12 comprises a composition that is substantially inert, that is, it maintains its physical and chemical integrity during the drug dispensing life of nicardipine from dosage form 10. The phrase, "maintains its physical and chemical integrity," means wall 12 does not lose its structure and it does not change during the dispensing life of dosage form 10, except for possible leaching of one or more components of the wall. Wall 12 comprises an internal surface facing the inside of compartment 15 and dosage form 10. Wall 12 comprises an external surface facing the environment of use.

Wall 12, in one presently preferred embodiment comprises a cellulose ethyl ether, or wall 12 comprises a composition comprising a cellulose ethyl ether, a cellulose ether, and other wall forming members. More specifically, wall 12 comprises from 45 weight percent (wt %) to 80 wt % of ethylcellulose, from 5 wt % to 30 wt % hydroxypropylcellulose and from 5 wt % to 30 wt % polyethylene glycol, with the total weight percent of all components comprising wall 12 equal to 100 wt %. In another specific embodiment, wall 12 comprises 45 wt % to 80 wt % of ethylcellulose, from 5 wt % to 30 wt % hydroxypropylcellulose, from 5 wt % to 30 wt % polyethylene glycol, and from 2 wt % to 20 wt % of polyvinyl pyrrolidone, with the total amount of all components comprising wall 12 equal to 100 wt %.

Wall 12, in another presently preferred embodiment comprises 100 wt % of a cellulose polymer comprising a member selected from the group consisting of a cellulose acylate, cellulose diacylate, cellulose triacylate, cellulose acetate, cellulose diacetate and cellulose triacetate. In another embodiment, wall 12 comprises a composition comprising from 60 wt % to 99 wt % of a member selected from the group consisting of a cellulose acylate, cellulose diacylate, cellulose triacylate, cellulose acetate, cellulose diacetate and cellulose triacetate, from 0 wt % to 35 wt % of a member selected from the group consisting of a cellulose ether selected from the group consisting of hydroxypropylcellulose and hydroxypropylmethylcellulose, and from 0 wt % to 30 wt % of polyethylene glycol, with the total amount of all components comprising wall 12 equal to 100 wt %.

Internal compartment 15, in drawing FIG. 2, comprises from 1 mg to 650 mg of the therapeutic drug nicardipine, represented by dots 16. The drug nicardipine 16 can be present in the form of its pharmaceutically acceptable salt, such as those formed by a member selected from the group consisting of an organic, inorganic, hydrochloric acid, hydrobromic acid, sulfonic acid, phosphoric acid, acetic acid, propionic acid, citric acid, oxalic acid, maleic acid, chlorotheophylline, gluconic acid, choline, or the like. Internal compartment 15 optionally comprises an osmagent 17, represented by dashes. The osmagents 17 are also known as osmotically effective solutes and as osmotically effective compounds. Osmagents 17 operable for the present purpose comprise water-soluble inorganic salts, sodium chloride, potassium chloride, potassium acid phosphate, tartaric acid, raffinose, water-soluble sugars, and the like. Generally compartment 15 optionally comprises from 1 mg to 75 mg of osmagent 17.

Figure 3:
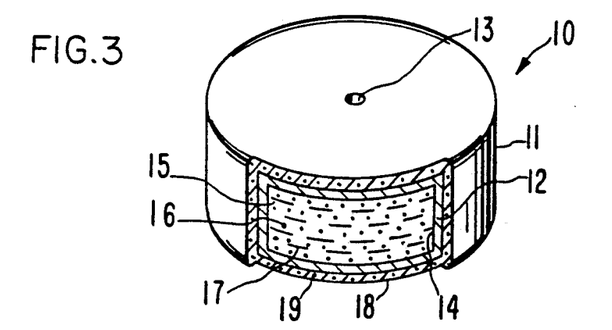
FIG. 3 is an opened view of the dosage form of FIG. 1 depicting the dosage form manufactured comprising means for providing immediate drug delivery of nicardipine and means for providing controlled and prolonged drug delivery of nicardipine.

FIG. 3 depicts another embodiment of dosage form 10, seen in opened section at 14. In drawing FIG. 3, dosage form 10 comprises body wall 11, wall 12, exit means 13, internal compartment 15, comprising from 1 mg to 650 mg of nicardipine 16 and osmotically effective compound 17. In FIG. 3, dosage form 10 comprises additionally an overcoat 18 coated onto the exterior surface of wall 12 comprising 1 mg to 100 mg of nicardipine. Overcoat 18 comprises, in a more preferred embodiment, a composition comprising from 1 mg to 55 mg of nicardipine and its non-toxic salts, and an aqueous soluble carrier comprising hydroxypropylmethylcellulose. Overcoat 18 makes available instantly the drug nicardipine. In operation, when dosage form 10 is in a fluid environment of use, overcoat 18 dissolves or undergoes dissolution and concurrently delivers nicardipine 19 to a nicardipine receptor.

Figure 4:
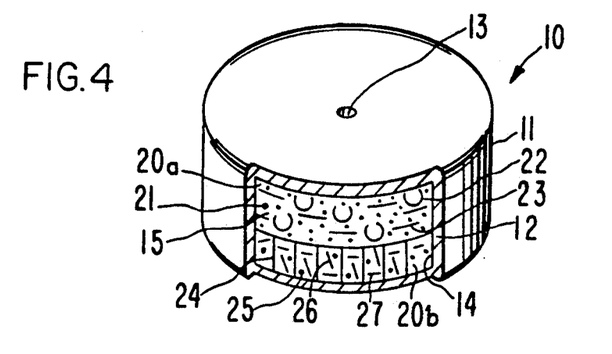
FIG. 4 is an opened view of the dosage form of FIG. 1 depicting a different structural embodiment of the dosage form provided by the invention.

In drawing FIG. 4, another dosage form 10 provided by the invention is seen in opened section. In FIG. 4, dosage form 10 comprises a body 11, wall 12, which wall 12 is sectioned at 14, with wall 12 surrounding and defining internal compartment 15. Wall 12 comprises at least one exit means 13 that connects compartment 15 with the exterior of dosage form 10. In dosage form 10, the internal compartment 15 comprises a first composition 20a, which also can be defined optionally as a first lamina 20a, and a second composition 20b, which also can be defined optionally as a second lamina 20b. First composition 20a and second composition 20b initially are in laminar arrangement and they cooperate with each other and with dosage form 10 for the effective delivery of nicardipine and its salts from dosage form 10.

In compartment 15, the first composition 20a comprises from 2 wt % to 50 wt % of nicardipine, or of nicardipine and its nontoxic salts, identified by 21; from 35 wt % to 85 wt % of polyethylene oxide identified by curved lines 22, which polyethylene oxide 22 comprises a member selected from the group consisting of a polyethylene oxide comprising a molecular weight of about 100,000, a polyethylene oxide having a molecular weight of about 200,000, a polyethylene oxide having a molecular weight of about 300,00, and a polyethylene oxide having a molecular weight of about 325,000, and in a more presently preferred embodiment comprises a polyethylene oxide having a 100,000 molecular weight blended with a polyethylene oxide having a 200,000 molecular weight, and blended with a polyethylene oxide having a 300,000 molecular weight, a polyethylene oxide comprising a 200,000 molecular weight blended with a polyethylene oxide having a 300,000 molecular weight, a polyethylene oxide having a 100,000 molecular weight blended with a polyethylene oxide having a 300,000 molecular weight and, a polyethylene oxide having a 100,000 molecular weight blended with a polyethylene oxide having a 200,000 molecular weight, and blended with a polyethylene oxide having a 300,000 molecular weight,; and from 0 wt % to 20 wt % of a hydroxypropylmethylcellulose having a number average molecular weight of 9,000 to 18,000, identified by dashes 23; which first composition 20a optionally comprises from zero weight percent to 3 wt % of a lubricant, such as zero weight percent to 3 wt % of magnesium stearate, with the total weight percent of all ingredients equal to 100 wt %.

The present invention provides first composition 20a in various embodiments, for example, (a) a composition comprising from 5 wt % to 100 wt % of a nicardipine, from 30 wt % to 70 wt % of a polyethylene oxide having a 100,000 molecular weight, from 10 wt % to 30 wt % of a polyethylene oxide having a 200,000 molecular weight, from 4 wt % to 7.5 wt % of a hydroxypropylmethylcellulose having a 11,300 molecular weight, and from 0 wt % to 7.5 wt % of a lubricant such as magnesium stearate; and (b) a composition comprising from 25 wt % to 75 wt % of nicardipine, from 20 wt % to 75 wt % of a polyethylene oxide having a 200,000 molecular weight, from 5 wt % to 30 wt % of a polyethylene oxide having a 300,000 molecular weight, from 4 wt % to 10 wt % of a hydroxypropylmethylcellulose having a molecular weight of 11,300 and from 0 wt % to 7.5 wt % of a lubricant, such as stearic acid. In compositions (a) and (b) the total weight percent of all ingredients is equal to 100 wt %.

The second composition 20b comprises from 50 wt % to 75 wt % of a polyethylene oxide comprising a 4,500,000 to 10,000,000 molecular weight, and more preferably from 4,500,000 to 5,500,000 molecular weight, identified by vertical lines 24; from 15 wt % to 35 wt % of an osmagent identified by dots 25; from 3 wt % to 15 wt % of a hydroxypropylmethylcellulose comprising a 9,000 to 18,000 molecular weight identified by slanted lines 26; from zero weight percent to 3 wt % of a lubricant, such as stearic acid, magnesium stearate or the like, identified by short dashes 27; and from zero weight percent to 3 wt % of a colorant, such as ferric oxide, with the total weight percent of all ingredients equal to 100 wt %.

The second composition 20b, in more specific embodiments comprises 60 wt % to 70 wt % of a polyethylene oxide comprising a 5,000,000 molecular weight, from 25 wt % to 35 wt % of osmagent sodium chloride, from 4 wt % to 6 wt % of a hydroxypropylmethylcellulose comprising a 11,300 molecular weight, from 0.75 wt % to 1.25 wt % ferric oxide, and from 0.4 wt % to 0.7 wt % magnesium stearate. The presence of the polyethylene oxide and the osmagent in the second composition increases the operating efficiency of dosage form 10. The operating efficiency occurs by the simultaneous hydration and swelling of the polyethylene oxide coupled with the osmotic imbibition of exterior fluid through the semipermeable wall by the osmagent at a rate dependent on the concentration gradient across the wall. These combined physical actions are maintained at a high level over a prolonged period of time, thereby enabling the second compositions to push the first composition at a more constant and uniform rate over a correspondingly prolonged period of time. The constant push against the first compartment assures a more uniform rate of release of nicardipine from the dosage form and concomitantly substantially prevents a declining and decreasing release rate over time.

Figure 13:
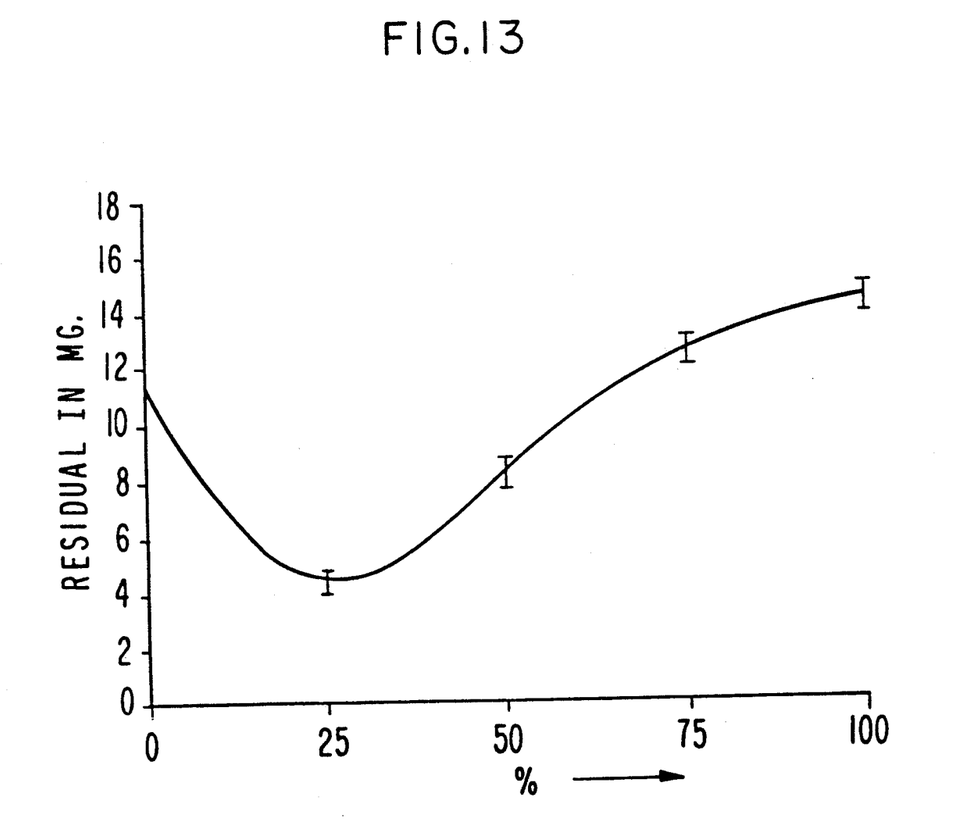
FIG. 13 depicts the total dose of nicardipine in the dose of nicardipine delivered less the residual amount of nicardipine in the dosage form comprising two polyethylene oxide polymers.

The present invention's use of two different polyethylene oxide polymers in the first composition 20a provide unexpected drug delivery for dosage form 10. That is, in prior art patent U.S. Pat. No. 4,783,337 issued to Wong et al, the drug delivery profile for a composition comprising nicardipine and a single polyethylene oxide having a 200,000 molecular weight resulted in a residual nicardipine in the dosage form in excess of 11.1%; also a dosage form provided by the prior art comprising nicardipine and sole polyethylene oxide having a 200,000 molecular weight leaves a residual concentration of 14.7% nicardipine in the dosage form. The present invention found that a dosage form comprising a composition of nicardipine and a blend of two different polyethylene oxide polymers exhibited as little as 6.8% residual nicardipine in the dosage form. This invention's improvement in nicardipine drug delivery is unforseen and it enhances significantly the use of the present dosage form for nicardipine therapy. With the present dosage form, both the physician and the patient know the latter is receiving substantially the intended nicardipine therapy. The accompanying drawing FIG. 13 demonstrates the beneficial results provided by the invention. In drawing FIG. 13, zero denotes the concentration of polyethylene oxide having a 200,000 molecular weight and a degree of polymerization of 4,540, and 100 denotes a polyethylene oxide having a 300,000 molecular weight and a 6,810 degree of polymerization. The invention provides blends of the polyethylene oxide polymers by using various percents listed on the x axis. The polyethylene oxides used for manufacturing dosage form 10 are commercially available from the Union Carbide Corporation, South Charleston, W.Va.

The expression, "exit means 13," as used herein, comprises means and methods suitable for the metered release of the beneficial drug nicardipine and/or its salts from dosage form 10. The means 13 includes at least one passageway, orifice, or the like, through wall 12 for communicating with composition 20a comprising nicardipine in dosage form 10. The expression, "at least one passageway," includes aperture, orifice, bore, pore, micropore, porous element through which the drug can diffuse or migrate, hollow fiber, capillary tube, porous overlay, porous insert, and the like. The expression also includes a material that erodes or is leached from wall 12 in the fluid environment of use to produce at least one passageway in dosage form 10. Representative materials suitable for forming at least one passageway, or a multiplicity of passageways, include an erodible poly(glycolic) acid or poly(lactic) acid member in the wall; a gelatinous filament; poly(vinyl alcohol); leachable materials such as a removable pore forming polysaccharide, salt, oxide, or the like. A passageway, or a plurality of passageways can be formed by leaching a pore-forming material such as sorbitol, lactose, maltose, or the like from the wall. The passageway can have any shape such as round, triangular, square, elliptical, or other irregular shapes, for assisting in the metered release of nicardipine from dosage form 10. Dosage form 10 can be constructed with one, or more passageways in spaced apart relations, on more than a single surface of a dosage form. Passageways are disclosed in U.S. Pat. Nos. 3,845,770 and 3,916,899 issued to Theeuwes and Higuchi; in U.S. Pat. No. 4,063,064 issued to Saunders and Mefford; and in U.S. Pat. No. 4,088,864 issued to Theeuwes, Saunders and Mefford. Passageways formed by leaching to form a pore of controlled delivery drug release are disclosed in U.S. Pat. Nos. 4,200,098 and 4,285,987 issued to Ayer and Theeuwes.

The osmagents used for the purpose of the present invention are also known as osmotically effective compounds and as osmotically effective solutes. The osmagents exhibit an osmotic pressure gradient across a semipermeable wall against an external fluid. The osmagent, along with the osmopolymer, imbibe fluid into the dosage form, thereby making available in situ fluid for imbibition and/or absorption by an osmopolymer to enhance its expansion for pushing the beneficial drug nicardipine from the dosage form. The osmagents can be inorganic or organic. Osmagents useful for the present purpose include magnesium sulfate, magnesium chloride, potassium sulfate, sodium sulfate, lithium sulfate, potassium acid phosphate, mannitol, sodium chloride, potassium chloride, urea, inositol, tartaric acid, raffinose, sucrose, glucose, sorbitol, and mixtures thereof. Osmagents are know to the prior art in U.S. Pat. No. 4,783,337.

The dosage form of the invention is manufactured by standard techniques. For example, in one embodiment, the drug nicardipine is mixed with the compositional forming ingredients and pressed into a lamina possessing dimensions that correspond to the internal dimensions of the space adjacent to the passageway of the dosage form. In another manufacturing embodiment, the drug nicardipine and other first composition forming ingredients and a solvent are mixed into a solid, or a semisolid by conventional methods such as ballmilling, calendering, stirring, or rollmilling, and then pressed into a preselected lamina forming shape. Next, a lamina of a composition comprising an osmopolymer and an osmagent are placed in contact with the lamina comprising the nicardipine, and the two lamina comprising the laminates are surrounded with a wall. The lamination of first composition 20a comprising the nicardipine and second composition 20b comprising the osmopolymer and the osmagent can be accomplished by using a conventional two-layered tablet press. The wall can be applied by molding, spraying, or dipping the pressed shapes into wall forming materials. Another and presently preferred technique that can be used for applying the wall is the air suspension coating procedure. This procedure consists in suspending and tumbling the two-layered laminate in a current of air until the wall forming composition surrounds the laminate. The air suspension procedure is described in U.S. Pat. No. 2,799,241; in *J. Am. Pharm. Assoc.*, Vol. 48, pp 451–459 (1979); and, ibid, Vol. 49, pp 82–84 (1960). Other standard manufacturing procedures are described in *Modern Plastic Encyclopedia*, Vol. 46, pp 62–70 (1969); and in *Pharmaceutical Sciences*, by Remington, 14th Ed., pp 1626–1978, (1970), published by Mack Publishing Co., Easton, Pa.

Exemplary solvents suitable for manufacturing the wall, the laminates include inert inorganic and organic solvents that do not adversely harm the nicardipine and other materials forming dosage form 10, and the final wall. The solvents broadly include a member selected from the group consisting of aqueous, alcohol, ketone, ester, ether, aliphatic hydrocarbon, halogenate, cycloaliphatic, aromatic heterocyclic solvents, mixtures thereof, and the like. Typical solvents include acetone, diacetone, alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, aqueous and nonaqueous mixtures, acetone and water, acetone and methanol, acetone and ethyl alcohol, methylene dichloride and methanol, ethylene dichloride and methanol, ethyl alcohol and water, and the like.

DETAILED DESCRIPTION OF EXAMPLES

The following examples are merely illustrative of the present invention and they should not be considered as limiting the scope of the invention in any way, as these examples and other equivalents thereof will become more apparent to those versed in the art in the light of the present disclosure, the drawings and the accompanying claims.

EXAMPLE 1

A dosage form adapted, designed and shaped as an osmotic drug delivery system was manufactured as follows: first, 1.92 kg of nicardipine hydrochloride was dry blended with 7.54 kg of polyethylene oxide comprising a 100,000 molecular weight, 1.88 kg of polyethylene oxide comprising a 200,000 molecular weight and 0.60 kg of hydroxypropylmethylcellulose comprising a 11,200 molecular weight for 15 minutes in a Hobart ® mixer. All the materials were pre-screened through a 30 mesh. Next, 7.5 liters of anhydrous ethyl alcohol was added to the blended materials, followed by 15 minutes of additional blending in the blender to yield a homogenous blend. Then, the wet mass was passed through a stainless steel screen with ¼ inch opening, about 6 mm, using a Fitzmill ® comminutor, at low speed. Next, the screened blend was dried in an oven at 70° F., about 22° C., for 20 hours. The dried granules were passed through a 14 mesh screen, and then 56 g of the lubricant magnesium stearate were added to yield 11,112 g of nicardipine drug granules.

In a separate operation, 16.125 kg of polyethylene oxide comprising a 5,000,000 molecular weight was mixed with 7.250 kg of sodium chloride, 1.25 kg of hydroxypropylmethylcellulose comprising a 11,200 molecular weight and optional 0.25 kg of red iron oxide added for color. The sodium chloride and the iron oxide were pre-screened through a 20 mesh screen. Then, 18 liters of anhydrous ethyl alcohol was added with mixing, followed by 15 minutes of additional mixing to produce a uniform blend. The wet mass was passed through a stainless steel screen with 6 mm opening using a Fluid Air ® mill at 500 rpm. Then, the granules were dried in a steam-heated oven at 22° C. for 70 hours. The dried granules were passed through a 10 mesh screen using a Fluid Air mill operating at 1500 rpm. Next, 120 g of magnesium stearate was added with blending to yield 24.02 kg of osmotic driving composition.

Figure 5:
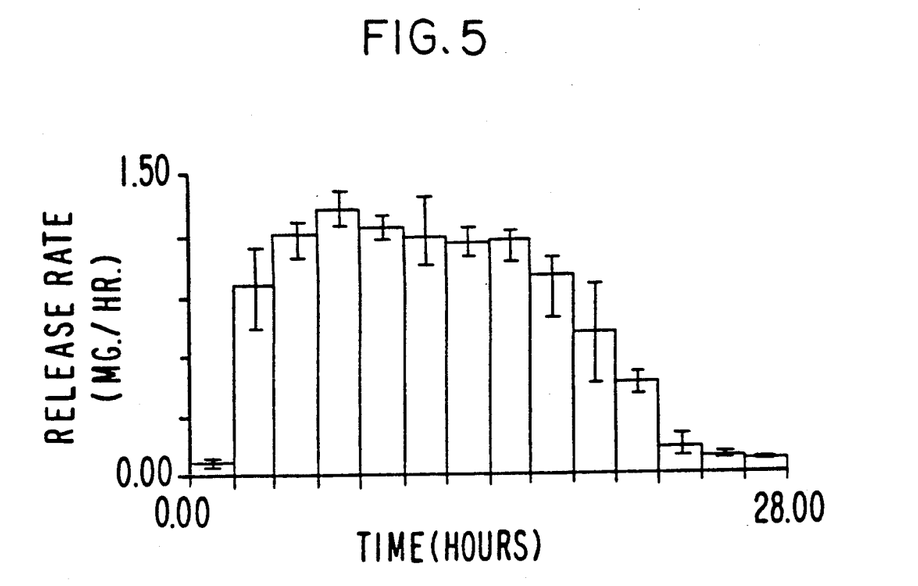
FIGS. 5 through 12 depict release rates and cumulative amounts of nicardipine delivered over time by dosage forms provided by the invention.
Figure 6:
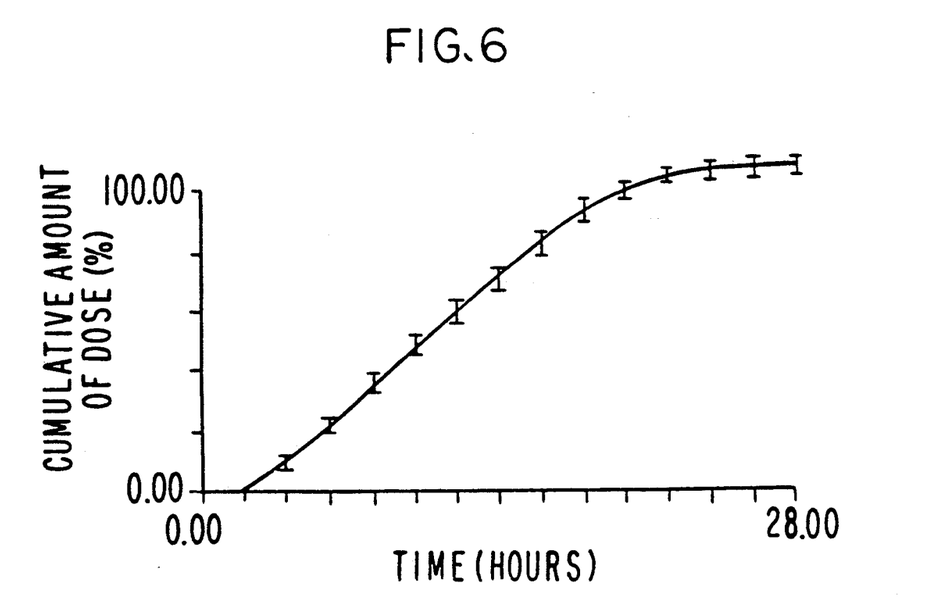

Next, the nicardipine drug granules and the osmotic driving composition were loaded into the hopper of a Kilian ® tablet press comprising a bilayer mode. Then, 12,857 tablets were compressed at an average weight of 239.2 mg each. The compressor speed was 21 rpm. The compressed, bilayer cores exhibited a hardness of 7-8 kp, and they were 11/32 inches, about 10 mm, in diameter. Then, 1,000 g of the bilayer cores were placed in a 6-inch, about 15 cm, truncated column and coated using a standard air suspension technique. The wall coating composition comprised 94% cellulose acetate comprising a 39.8% acetyl content and 6% polyethylene glycol 3350 dissolved in a 4% (weight/weight) solution in 90% methylene chloride/10% methanol (w/w). About 3,600 g of coating solution was applied to the bilayer cores. The wet weight gain for each core was 35.7 mg. A 25 mil passageway was laser drilled in each coated core. Then, the dosage forms were dried at 45° C. and 45% relative humidity for 70 hours, followed by 3 hours at 45° C. without humidity. The dry membrane weight is about 30 mg. The final dosage forms comprised 21.10 mg of nicardipine hydrochloride. The release rate in mg/hr. and the cumulative amount of nicardipine release over a prolonged period of 28 hours is seen in accompanying FIG. 5 and FIG. 6.

EXAMPLE 2

The procedure set forth in Example 1 was followed in this example. The composition comprising a member selected from the group comprising the drug nicardipine and its therapeutically acceptable salts used in this example was prepared according to Example 1. The osmotic driving composition was prepared as described, and in this example the osmotic driving composition comprises 64.5% polyethylene oxide Coagulant ® possessing a 5,000,000 molecular weight, 29% of sodium chloride, 5% of hydroxypropylmethylcellulose possessing a 11,200 molecular weight, 1% of iron oxide, and 0.5% of stearic acid. The drug nicardipine composition and the osmotic driving composition were compressed under 2.25 tons of compression force into bilayer cores.

Figure 7:
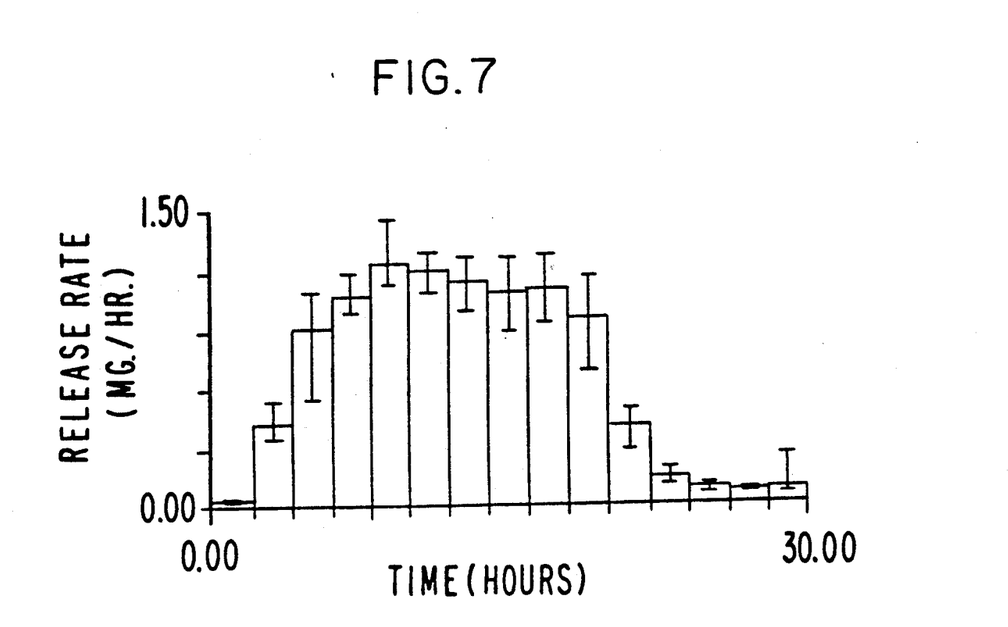
Figure 8:
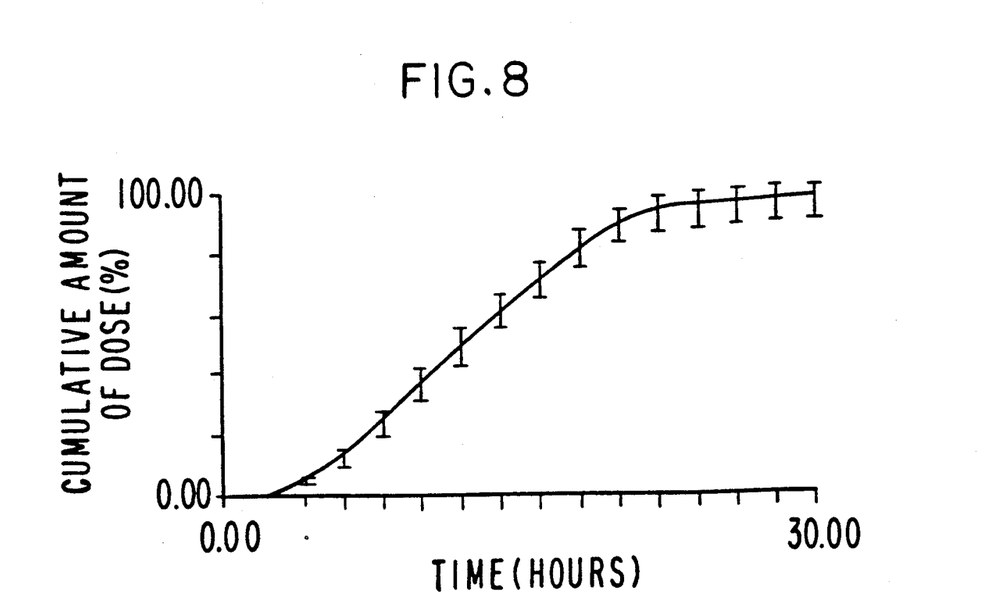

Next, 1,000 g of the bilayer cores were coated in a Wurster ® air suspension coater. The coating solution comprises 241.4 g of ethyl cellulose, 62.2 g of hydroxypropylcellulose and 62.2 g of polyethylene glycol all dissolved in 10,000 ml of anhydrous ethyl alcohol and 877.8 ml of sterile water. The bilayers were coated at a flow rate of 38-40 ml/min. until the bilayers were uniformly coated with the wall forming composition. The average coat applied to each bilayer was about 37.1 mg. The coated bilayers were laser drilled to effect a 24 mil passageway in each drug delivery system. The delivery systems were dried for 72 hours at 50° C. and the average dry wall weighed about 33.5 mg. Each drug delivery system comprised 22 mg of nicardipine hydrochloride. The release rate in mg/hr., and the cumulative amount released over an extended period of time are seen in accompanying FIG. 7 and FIG. 8.

EXAMPLE 3

The procedure of Examples 1 and 2 was followed in this example, with the conditions as previously set forth, except that in the present example the wall forming composition comprises 280.9 g of ethyl cellulose, 70 g of hydroxypropylcellulose, 70 g of polyethylene glycol, 12,000 ml of anhydrous ethyl alcohol and 1.053 l of sterile water. The dosage form comprised a dry wall of 44.8 mg and a passageway of 23.6 mil.

EXAMPLE 4

Figure 9:
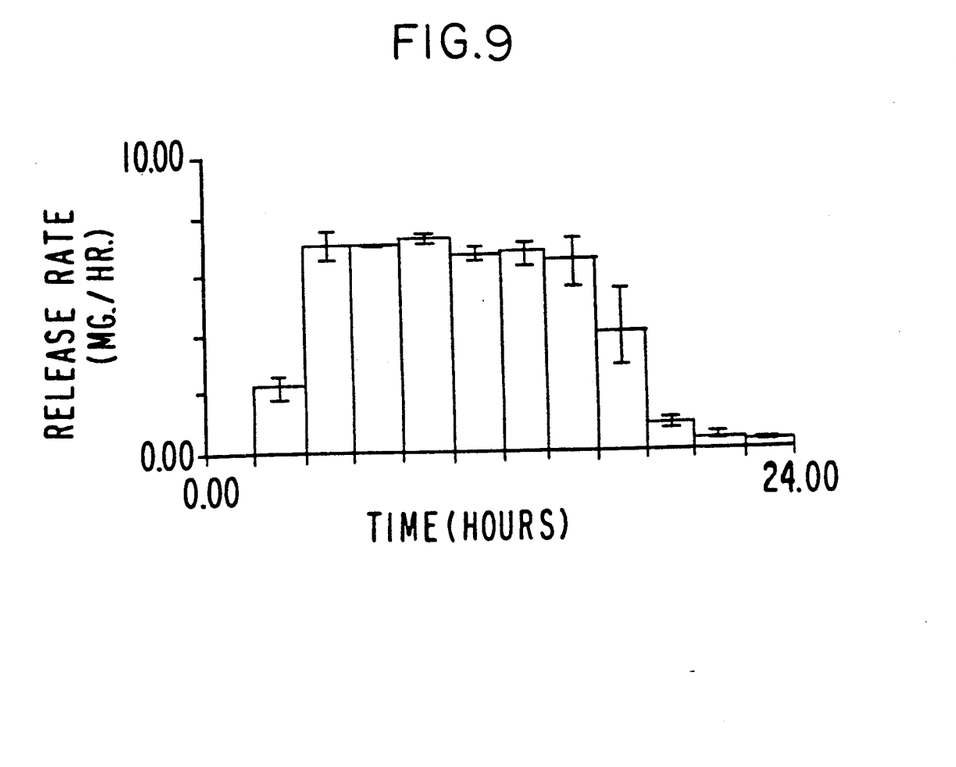
Figure 10:
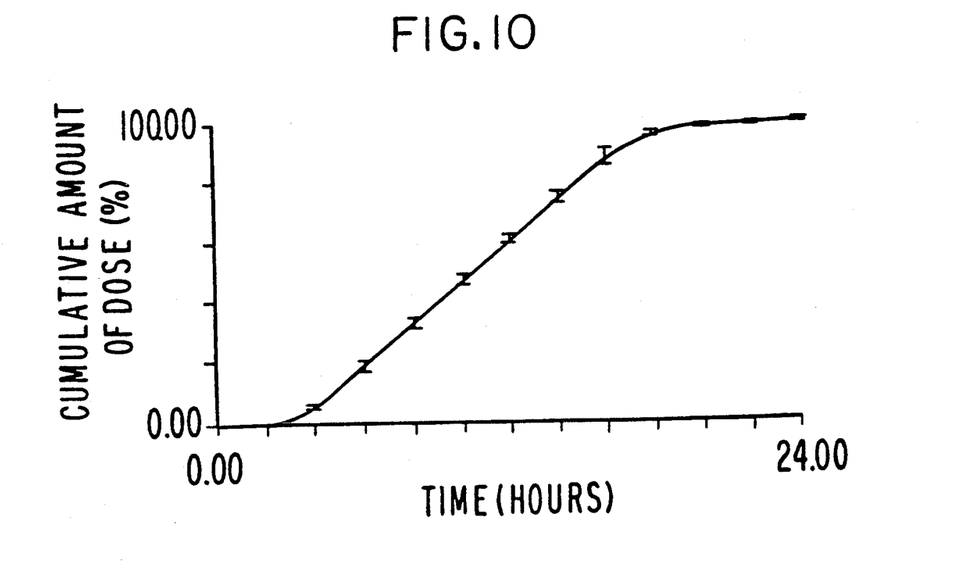

The procedure of Examples 1 and 2 were followed in this example, with all procedures as previously described, except that in this example the drug layer comprises 40 wt % nicardipine hydrochloride, 46.33 wt % polyethylene oxide with a 200,000 molecular weight, 8.18 wt % polyethylene oxide, having a 300,000 molecular weight, 5 wt % hydroxypropylcellulose, and 0.50 wt % of calcium stearate. The osmotic driving composition comprised 64.50 wt % polyethylene oxide coagulant possessing a 5,000,000 molecular weight, 29 wt % of sodium chloride, 5 wt % hydroxypropylmethylcellulose possessing a 11,200 molecular weight, 1 wt % ferric oxide, and 0.5 wt % calcium stearate. The wall of the dosage form comprises 60 wt % ethyl cellulose, 20 wt % hydroxypropylcellulose and 20 wt % polyethylene glycol. The dosage form comprises a 0.76 mm orifice, and exhibited a rate of release and cumulative amount release as seen in FIG. 9 and FIG. 10.

EXAMPLE 5

Figure 11:
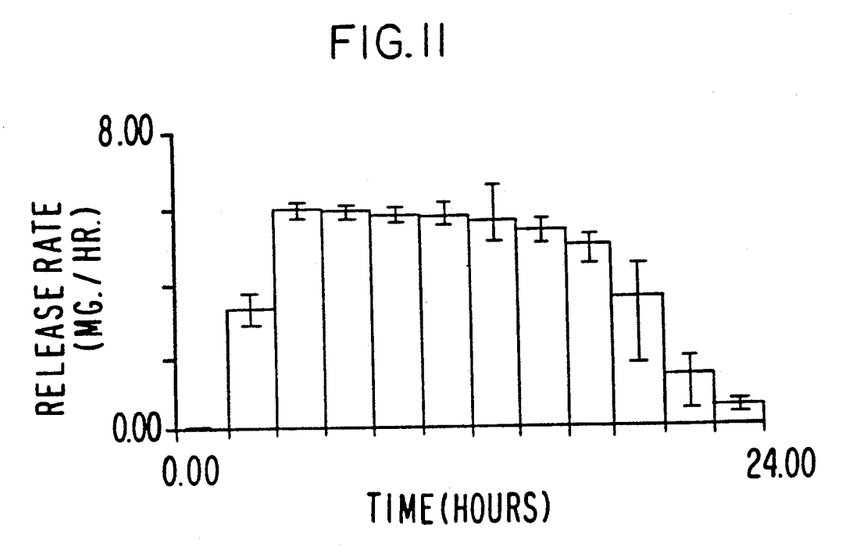
Figure 12:
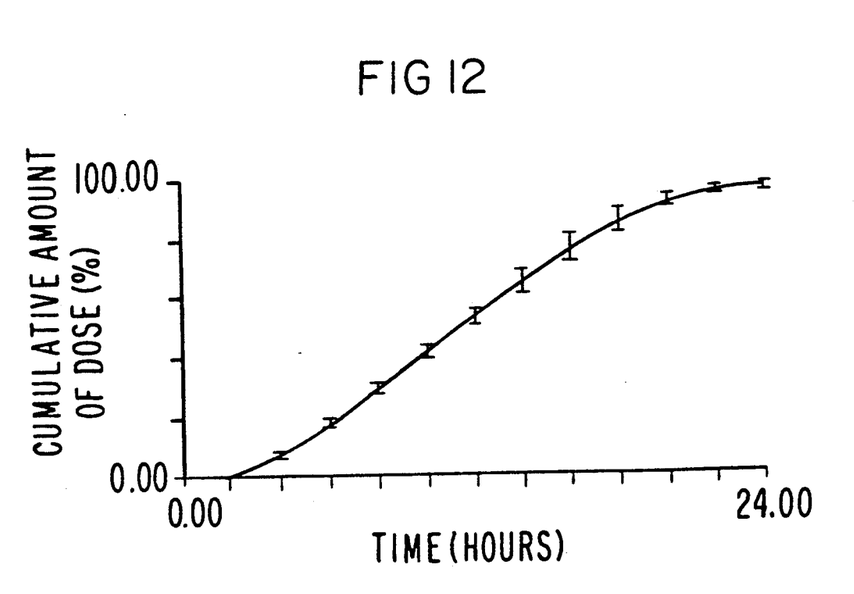

The procedures set forth herein were followed in this example, wherein the drug layer comprises 110 mg of nicardipine hydrochloride, 127.4 mg of polyethylene oxide having a 200,000 molecular weight, 22.5 mg of polyethylene oxide having a 300,000 molecular weight, 13.7 mg of hydroxypropylmethylcellulose having a 11,200 molecular weight, and 1.4 mg of magnesium stearate. The osmotic driving composition comprises 118.7 mg of polyethylene oxide having a molecular weight of 5,000,000, 53.4 mg of sodium chloride, 9.2 mg of hydroxypropyl- methylcellulose having a 11,200 molecular weight, 1.8 mg of ferric oxide, and 0.9 mg of magnesium stearate. The wall of the dosage form comprises 45.1 mg of cellulose acetate having a 39.8% acetyl content and 5 mg of polyethylene glycol. The dosage form comprises a 0.79 mm orifice and exhibits a release rate and a cumulative amount released over time curves as seen in FIG. 11 and FIG. 12.

EXAMPLE 6

A dosage form comprising 110 mg of nicardipine hydrochloride was prepared by following the above procedures. A cellulose acetate wall was coated from a 90:10 (w/w) methylene chloride/methanol cosolvent. The wall composition was 45.1 mg of cellulose acetate having a 39.8% acetyl content, and 5.0 mg of polyethylene glycol 3350. The dosage form released 85 mg of the nicardipine hydrochloride in 18.1 hours. The dosage form had a zero order release rate of 5.7 mg/hour, through a single orifice.

EXAMPLE 7

A series of dosage forms are prepared for delivery of nicardipine at a controlled rate orally to a warm-blooded animal in need of nicardipine therapy. The dosage forms are administered according to the method comprising the steps of: (A) admitting into a warm-blooded animal a dosage form comprising: (1) a wall surrounding a compartment, the wall selected from the group of walls consisting of a composition comprising: (a) 20 mg to 30 mg of ethyl cellulose, 4 mg to 10 mg of hydroxypropylcellulose and 4 mg to 10 mg of polyethylene glycol; (b) a composition comprising 30 mg to 40 mg of ethyl cellulose, 10 mg to 15 mg of hydroxypropylcellulose and 10 mg to 15 mg of polyethylene glycol; (c) a composition comprising 15 mg to 25 mg of a cellulose acetate and 0.5 mg to 2 mg of polyethylene glycol; and, (d) a composition comprising 40 mg to 50 mg of cellulose acetate and 3 mg to 10 mg of polyethylene glycol; (2) (a) a drug compositional layer in the compartment comprising nicardipine in a dose amount of 1 mg to 20 mg for performing a therapeutic program of treating of angina pectoris and hypertension, from 70 mg to 90 mg of a polyethylene oxide comprising a 100,000 molecular weight, from 15 to 30 mg of a polyethylene oxide comprising a 200,000 molecular weight, from 4 to 7.5 mg of a hydroxypropylmethylcellulose comprising a 11,200 molecular weight and 0.1 to 1 mg of magnesium stearate; (b) a drug composition comprising 20 mg to 100 mg of nicardipine and its salts, at least members selected from the group consisting of a polyethylene oxide having a 100,000 molecular weight, a polyethylene oxide having a 200,000 molecular weight and a polyethylene oxide having a 300,000 molecular weight with ratio of the two polyethylene oxides 30 to 90 parts of the lower molecular weight to 10 to 7 parts of the higher molecular weight; (c) a drug composition comprising 18 mg to 30 mg of nicardipine, from 80 mg to 90 mg of polyethylene oxide having a 200,000 molecular weight, from 15 mg to 25 mg of a polyethylene oxide having a 300,000 molecular weight, from 5 mg to 8 mg of hydroxypropylmethylcellulose, and from 0.5 mg to 1.5 mg of polyeth compositional layer in the compartment comprising nicardipine present in an amount for performing a therapeutic program, said composition comprising from 105 to 115 mg of nicardipine, from 120 mg to 130 mg of a polyethylene oxide having a 200,000 molecular weight, from 18 mg to 28 mg of a polyethylene oxide having a 300,000 molecular weight, from 10 mg to 15 mg of a hydroxypropylmethylcellulose having a 11,200 molecular weight, and from 0.4 mg to 1.8 mg of magnesium stearate: (e) a drug composition 150 to 163 mg of nicardipine hydrochloride, 171 mg of polyethylene oxide having a 200,000 molecular weight, 30.4 mg of polyethylene oxide having a 300,000 molecular weight, 18.5 mg of hydroxypropylmethylcellulose and 1.8 mg of calcium stearate; (f) a nicardipine composition from 120 to 130 mg of nicardipine, 133 mg of polyethylene oxide having a 200,000 molecular weight, 24 mg of polyethylene oxide having a 300,000 molecular weight, 14.4 mg of hydroxypropyl- methylcellulose having a 11,200 molecular weight and 1.4 mg of magnesium stearate: and (g) a nicardipine sulfate composition comprising a polyethylene oxide having a 200,000 molecular weight, and a polyethylene oxide comprising a 300,000 molecular weight; (3) (a) a compositional layer in the compartment for pushing the nicardipine composition from the dosage form, said pushing composition comprising from 60 mg to 70 mg of a polyethylene oxide coagulant having a 5,000,000 molecular weight, from 25 mg to 25 mg of sodium chloride, from 3 mg to 8 mg of hydroxypropylmethylcellulose having a 11,200 molecular weight, from 0.5 mg to 1.5 mg of ferric oxide and from 0.2 mg to 0.75 of magnesium stearate; (b) a push composition comprising 110 mg to 125 mg of polyethylene oxide coagulant having a 5,000,000 molecular weight, from 50 mg to 55 mg of sodium chloride, from 6 mg to 12 mg of hydroxypropylmethylcellulose having a 11,200 molecular weight, from 1 mg to 3 mg of ferric oxide and from 0.7 mg to 1.5 mg of magnesium stearate; and (4) at least one passageway in the wall for releasing the nicardipine; (B) imbibing fluid through the semipermeable part of the wall predicated on the osmotic pressure gradient across the semipermeable wall, thereby causing the nicardipine drug layer to hydrate and reduce in viscosity and simultaneously causing the osmotic push composition to absorb water, thereby expand, and push the nicardipine from the dosage form; and (C) delivering the therapeutic nicardipine from the dosage form through the exit passageway to the warm-blooded animal over a prolonged period of time.

EXAMPLE 8

An osmotic tablet for administering a member selected from the group consisting of nicardipine and its pharmaceutically acceptable salts for its antihypertensive therapy followed by its diuretic and natriuretic pharmacodynamic effects is manufactured as follows: first, a nicardipine drug layer is granulated using a Glatt ® bed granulator equipped with a 90 kg bowl. The bowl is charged with 37 kg of nicardipine, 41.7 kg of polyethylene oxide possessing a 200,000 molecular weight and 7.4 kg of polyethylene oxide possessing a 300,000 molecular weight. Next, a granulation fluid comprising 1.8 kg of hydroxypropylmethylcellulose comprising a 11,200 molecular weight dissolved in purified water is added to the granulation bowl. Then, 0.4 kg of magnesium stearate is added as a lubricant and granulation carrier out for 10 minutes.

Next, an osmotic composition comprising granules is formed by mixing 73.5 kg of polyethylene oxide comprising a 7,500,000 molecular weight and 20 kg of sodium chloride with 1 kg of iron oxide and 2 kg of hydroxypropylmethylcellulose comprising a 11,200 molecular weight. Then, 3 kg of hydroxypropylmethylcellulose in distilled water is sprayed onto the fresh mix to form granules. After drying, 0.5 kg of magnesium stearate is incorporated into the granular bath.

Next, a 60 mg tablet is prepared comprising 69 mg of the expandable, osmotic hydrogel composition and 137.5 mg of the nicardipine composition. The two layers comprising the tablet are coated with a solution of cellulose acetate comprising 39.8% acetyl groups and polyethylene glycol in a 93:7 ratio. The solvent system comprises 95% acetone and 5% distilled water. The coating composition comprises a solid content of 6%. The tablets are coated in a pan coater. Then, the coated osmotic tablets are drilled with a laser to effect a 25 mil hole. The systems are air dried to remove all residual solvent.

Then, 10 mg of nicardipine is applied in an aqueous suspension comprising 15% solids as an exterior instant nicardipine coat. The aqueous suspension comprises 30% hydroxypropylmethylcellulose E-5 comprising a 11,300 molecular weight and 20% hydroxypropylmethylcellulose E-15 LV comprising a 15,900 molecular weight. Then, the aqueous nicardipine is coated with a light blue protective coat and the identifying dose of the nicardipine printed thereon. The latter coatings are applied with a Vector ® pan coater.

EXAMPLE 9

An osmotic dosage form comprising 90 mg of nicardipine is prepared following the above procedures. The core of the dosage form, prepared according to this example, is prepared by tabletting 103 mg of the expandable, hydrophilic granules and 206 mg of nicardipine granules, which are pressed into contacting layers. The core is coated with a semipermeable wall-forming composition comprising cellulose acetate comprising a 39.8% acetyl content and polyethylene glycol in a 93:7 ratio. The solvent system for coating the wall comprises 95% acetone, 5% water and 6% solids. The cores weigh 240 kg and the cores are coated in a pan coater. Next, the coated cores are drilled using a laser to produce a 25 mil hole. After drying, 15 mg of nicardipine is coated in an aqueous suspension to the exterior of the cellulose acetate wall. The 15 mg of nicardipine is applied in an aqueous suspension comprising 15% solids, consisting of 50% nicardipine, 30% hydroxypropylmethylcellulose E-5 comprising a 11,300 molecular weight and 20% hydroxypropylmethylcellulose E-15 LV comprising a 15,900 molecular weight. The percents are in weight percent. The nicardipine is coated with an outermost coat of a light blue coat. The coats are applied with a Vector ® pan coater.

EXAMPLE 10

An osmotic dosage form comprising 120 mg of nicardipine is prepared by following the above example, wherein all conditions are as set forth, except for the following: a core is prepared comprising 145 mg of osmotic granules comprising the 7,500,000 molecular weight polyethylene oxide and 289 mg of the nicardipine granules. The core is coated with a semipermeable wall comprising cellulose acetate comprising a 39.8% acetyl content, and polyethylene glycol in a 93:7 ratio. The wall coating solvent comprises 95% acetone and 5% water with a 6% solid content. The cores are coated in a pan coater. The cellulose acetate cores are laser drilled to form a 25 mil dispensing orifice. Next, 15 mg is applied as an aqueous suspension comprising 15% solids, by weight, consisting of 50% nicardipine, 30% hydroxypropylmethylcellulose E-5 comprising a 11,300 molecular weight, and 20% hydroxypropylmethylcellulose E-15 LV comprising a 15,900 molecular weight. The coating is applied with a pan coater. In a biological environment, the exterior coat provides immediate nicardipine for immediate therapy.

In summary, it will be appreciated that the present invention contributes to the art an unobvious dosage form that possesses practical utility, and can administer nicardipine at a dose metered release rate per unit time. While the invention has been described and pointed out in detail with reference to operative embodiment thereof, it will be understood by those skilled in the art that various changes, modifications, substitutions and omissions can be made without departing from the spirit of the invention. It is intended therefore, that the invention embraces equivalents within the scope of the claims which follow.

We claim:
1. An improvement in a method for administering nicardipine to a patient in need of nicardipine therapy, wherein the method comprises:
(A) admitting into a patient a dosage form comprising:
(1) a wall comprising an interior and an exterior surface, said wall comprising a composition permeable to the passage of fluid, which wall surrounds;
(2) a compartment;
(3) a push composition in the compartment comprising a polyethylene oxide possessing a 4,500,000 to 10,000,000 molecular weight for imbibing fluid and expanding in the compartment;
(4) a passageway in the wall that connects the exterior with the interior of the dosage form, and wherein the improvement in the dosage form comprises:
(5) a drug composition in the compartment comprising from 1 mg to 650 mg of a member selected from the group consisting of nicardipine and its therapeutically acceptable salts, a member selected from the group consisting of polyethylene oxide comprising a 200,000 molecular weight and a polyethylene oxide comprising a 300,000 molecular weight, which polyethylene oxide acts with the push composition to deliver a substantially maximum dose of nicardipine from the dosage form; and
(6) a drug composition comprising 1 to 100 mg of a member selected from the group consisting of nicardipine and its pharmaceutically acceptable salts releasably coated on the exterior surface of the wall for providing immediate nicardipine therapy;
(B) letting fluid contact the exterior nicardipine coat for releasing the coat for providing 1 mg to 100 mg of immediate nicardipine therapy to the patient;
(C) letting fluid enter the dosage form for (a) contacting the composition in the compartment comprising nicardipine for providing an administrable nicardipine composition, and for (b) contacting the push composition causing it to expand and push nicardipine through the exit passageway; thereby
(D) delivering a therapeutically effective amount of 1 mg to 650 mg of nicardipine from the dosage form to the patient.

2. An improvement in a dosage form for administering nicardipine a patient for its antihypertensive effects followed by its diuretic and natriuretic effects, wherein the dosage form comprises:
(a) a wall comprising an inside surface and an exterior surface, said wall comprising from 20 mg to 30 mg of ethyl cellulose, from 4 mg to 10 mg of hydroxypropylcellulose and 4 mg to 10 mg of polyethylene glycol, which wall surrounds;
(b) a compartment;
(c) a push composition in the compartment comprising a polyethylene oxide possessing a 4,500,000 to 10,000,000 molecular weight for imbibing fluid and expanding in the compartment;
(d) a passageway in the wall that connects the exterior with the interior of the dosage form, and wherein the improvement comprises in the compartment;

(e) a nicardipine composition comprising from 1 mg to 650 mg of a member selected from the group consisting of nicardipine and its therapeutically acceptable salts, and a member selected from the group consisting of polyethylene oxide comprising a 100,000 molecular weight, and a polyethylene oxide comprising a 200,000 molecular weight, which polyethylene oxide acts together with the push composition to deliver substantially a maximum dose of nicardipine from the dosage form; and, (f) a nicardipine composition comprising 1 mg to 100 mg of a member selected from the group consisting of nicardipine and its pharmaceutically acceptable salts on the exterior of the wall to deliver an immediate dose of nicardipine from the dosage form.

* * * * *

UNITED STATES PATENT AND TRADEMARK OFFICE
CERTIFICATE OF CORRECTION

PATENT NO. : 5,186,942
DATED : February 16, 1993
INVENTOR(S) : Joseph C. Deters, David R. Swanson, Stephen C. DeRosa It is certified that error appears in the above-identified patent and that said Letters Patent is hereby corrected as shown below:

Cover page column 1 in the Notice: section, line 10, "Mar. 7, 2009" should read --March 17, 2009--.

Signed and Sealed this

Twenty-fifth Day of May, 1993

Attest:

MICHAEL K. KIRK

Attesting Officer     Acting Commissioner of Patents and Trademarks